(12) United States Patent
Shibasaki et al.

(10) Patent No.: US 8,940,919 B2
(45) Date of Patent: Jan. 27, 2015

(54) COMPOUND, METHOD FOR PRODUCING THE SAME, AND METHOD FOR PRODUCING OSELTAMIVIR PHOSPHATE

(71) Applicant: Microbial Chemistry Research Foundation, Tokyo (JP)

(72) Inventors: Masakatsu Shibasaki, Tokyo (JP); Kenzo Yamatsugu, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 14/017,574

(22) Filed: Sep. 4, 2013

(65) Prior Publication Data

US 2014/0046087 A1  Feb. 13, 2014

Related U.S. Application Data

(63) Continuation of application No. PCT/JP2012/055085, filed on Feb. 29, 2012.

(30) Foreign Application Priority Data

Mar. 8, 2011 (JP) ................................. 2011-050720

(51) Int. Cl.
| | | |
|---|---|---|
| C07C 229/00 | (2006.01) | |
| C07C 229/48 | (2006.01) | |
| C07B 53/00 | (2006.01) | |
| C07C 229/30 | (2006.01) | |
| C07C 229/34 | (2006.01) | |
| C07C 229/60 | (2006.01) | |
| C07C 269/06 | (2006.01) | |
| C07C 271/24 | (2006.01) | |

(52) U.S. Cl.
CPC .............. *C07C 229/48* (2013.01); *C07B 53/00* (2013.01); *C07C 229/30* (2013.01); *C07C 229/34* (2013.01); *C07C 229/60* (2013.01); *C07C 269/06* (2013.01); *C07C 271/24* (2013.01); *C07C 2101/16* (2013.01)
USPC ........................................................... 560/39

(58) Field of Classification Search
CPC .. C07C 269/06; C07C 271/24; C07C 101/16; C07C 229/30; C07C 229/34; C07C 229/48; C07C 229/60; C07B 53/00
USPC ............................................... 560/19, 39, 171
See application file for complete search history.

(56) References Cited

PUBLICATIONS

Lie et al. 2009 (Copper-Catalyzed Amine-Alkyne-Alkyne Addition Reaction: An Efficient Method for the Synthesis of gamma delta-Alkynyl-Beta-Amino Acid Derivatives, Chem. Eur. J. 15, 11668-11674, 2009).*

Lei et al. 2008 (Efficient Synthesis of gamma delta-Alkynyl-Beta-Amino Acid Derivatives by New Copper-Catalyzed Amine-Alkyne-Alkyne Addition Reaction, Adv. Synth. Catal. 350 2226-2230, 2008).*

Loukas et al, (Efficient Protocols for the Synthesis of Enantiopure Omega Amino Acids with Proteinogenic Side Chains, J, of Peptide Science, 9, 312-319, 2003).*

Murray et al. (Synthesis of densely functionalized pyrrolidinone templates by an intramolecular oxo-Diels—Alder reaction, Tetrahedron Letters vol. 43, pp. 7389-7392, 2002).*

Dragovich et al. (Solid-phase Synthesis of Irreversible Human Rhinovirus 3C Protease Inhibitors. Part 1: Optimization of Tripeptides Incorporating N-terminal Amides, Bioorganic & Medicinal Chemistry, vol. 7, pp. 589-598, 1999).*

Zhong-Yong (A Regioselective Tandem Reduction-Wittig-Horner Reaction Involving the alpha-Ester Moiety of Diethyl Aspartate or Glutamate Tetrahedron Letters vol. 35, No. 15, pp. 2305-2308, 1994).*

Kim, C.U., et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," J. Am. Chem. Soc., vol. 119, No. 4, 1997, pp. 681-690.

Yeung, Y.Y., et al., "A Short Enantioselective Pathway for the Synthesis of the Anti-Influenza Neuramidase Inhibitor Oseltamivir from 1,3-Butadiene and Acrylic Acid," J. Am. Chem. Soc., vol. 128, No. 19, 2006, pp. 6310-6311.

(Continued)

*Primary Examiner* — Brandon Fetterolf
*Assistant Examiner* — Blaine G Doletski
(74) *Attorney, Agent, or Firm* — Carmody Torrance Sandak & Hennessey LLP

(57) ABSTRACT

A compound represented by the following general formula (1), and a method for producing the compound represented by the general formula (1), the method comprising: reacting together a compound represented by the following general formula (2), a compound represented by the following general formula (3), and a compound represented by the following general formula (4):

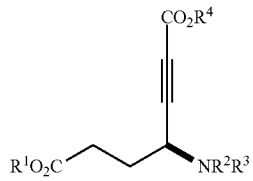

General Formula (1)

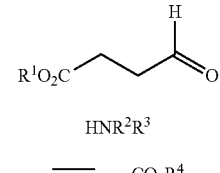

General Formula (2)

General Formula (3)

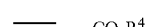

General Formula (4)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

3 Claims, 4 Drawing Sheets

(56) References Cited

PUBLICATIONS

Loukas, V. et al., "Efficient Protocols for the Synthesis of Enantiopure γ-Amino Acids with Proteinogenic Side Chains," Journal of Peptide Science, vol. 9, No. 5, 2003, pp. 312-319.

Murray, W.V., et al., "Synthesis of Densely Functionalized Pyrrolidinone Templates by an Intramolecular oxo-Diels-Alder Reaction," Tetrahedron Letters, vol. 43, No. 41, 2002, pp. 7389-7892.

Dragovich, P.S., et al., "Structure-Based Design, Synthesis, and Biological Evaluation of Irreversible Human Rhinovirus 3C Protease Inhibitors. 2. Peptide Structure—Activity Studies," Journal of Medicinal Chemistry, vol. 41, No. 15, 1998, pp. 2819-2834.

Kipassa, N.T., et al., "Efficient Short Step Synthesis of Corey's Tamiflu Intermediate," Organic Letters, vol. 10, No. 5, 2008, pp. 815-816.

Bromfield, K.M., et al., "An Iron Carbonyl Approach to the Influenza Neuraminidase Inhibitor Oseltamivir," Chemical Communications, (Cambridge, U.K.), No. 30, 2007, pp. 3183-3185.

Misiti, D. et al., "Selective Catalytic Hydrogenation of γ-amino α, β-Unsaturated Esters in the Presence of Hydrogenable Protecting Groups," Synthesis (1999), No. 5, pp. 873-877.

* cited by examiner

COMPOUND, METHOD FOR PRODUCING THE SAME, AND METHOD FOR PRODUCING OSELTAMIVIR PHOSPHATE

CROSS-REFERENCE TO RELATED APPLICATION

This application is a continuation application of International Application PCT/JP2012/055085 filed on Feb. 29, 2012 and designated the U.S., the entire contents of which are incorporated herein by reference.

BACKGROUND OF THE INVENTION

1. Field of the Invention

The present invention relates to a compound and a method for producing the same, and a method for producing oseltamivir phosphate.

2. Description of the Related Art

There is concern that mutation of an avian influenza virus results in a pandemic of new influenza, for example, H5N1 to cause a number of deaths. Oseltamivir phosphate (trade name "Tamiflu"), which is an antiviral drug, is known to exhibit a remarkable response to new influenza, and the state institutions increasingly stockpile such a drug for infection prevention. Therefore, the demand for oseltamivir phosphate is rapidly increased across the world and there is a demand for developing a measure for inexpensively supplying oseltamivir phosphate in a large amount.

As a method for synthesizing oseltamivir phosphate, a method of using shikimic acid as a starting material is known (see, for example, J. Am. Chem. Soc., 119, 681, 1997).

However, shikimic acid is prepared by extraction or purification from *Illicium verum* fruits (star anise), or via fermentation from D-glucose by *E. coli*, and there is a problem that such processes are time-consuming and costly. In addition, it is sometimes difficult to supply plant materials such as *Illicium verum* fruits stably. Accordingly, there is a demand for developing a measure for efficiently chemically synthesizing oseltamivir phosphate from an easily available raw material compound.

For example, a method for synthesizing oseltamivir phosphate from 1,3-butadiene and acrylic acid, and an intermediate in the synthesis method have been proposed (see, for example, J. Am. Chem. Soc., 128, 6310, 2006).

In addition, another method for synthesizing an intermediate leading to the synthesis of oseltamivir phosphate described in J. Am. Chem. Soc., 128, 6310, 2006, which is a diene compound (compound A illustrated in FIG. 1), has been proposed (see, for example, Org. Let., 2008, 10, 815 and FIG. 1).

However, such techniques proposed cannot be said to be sufficient from industrial aspect, because there are problems that, for example, the synthesized product is a racemic form, and a thiol compound having a high toxicity is stoichiometrically used.

Accordingly, there is currently a demand for providing an intermediate useful for industrially producing oseltamivir phosphate.

SUMMARY OF THE INVENTION

A problem of the present invention is to solve the conventional problems to achieve the following object. That is, an object of the present invention is to provide an intermediate useful for industrially producing oseltamivir phosphate.

A measure for solving the above problem is as follows. That is, a compound of the present invention is represented by the following general formula (1):

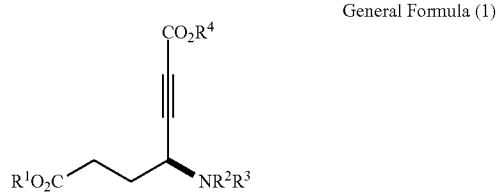

General Formula (1)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

According to the present invention, it is possible to solve the conventional problems to achieve the object, thereby providing an intermediate useful for industrially producing oseltamivir phosphate.

DETAILED DESCRIPTION OF THE INVENTION

Figure 1:
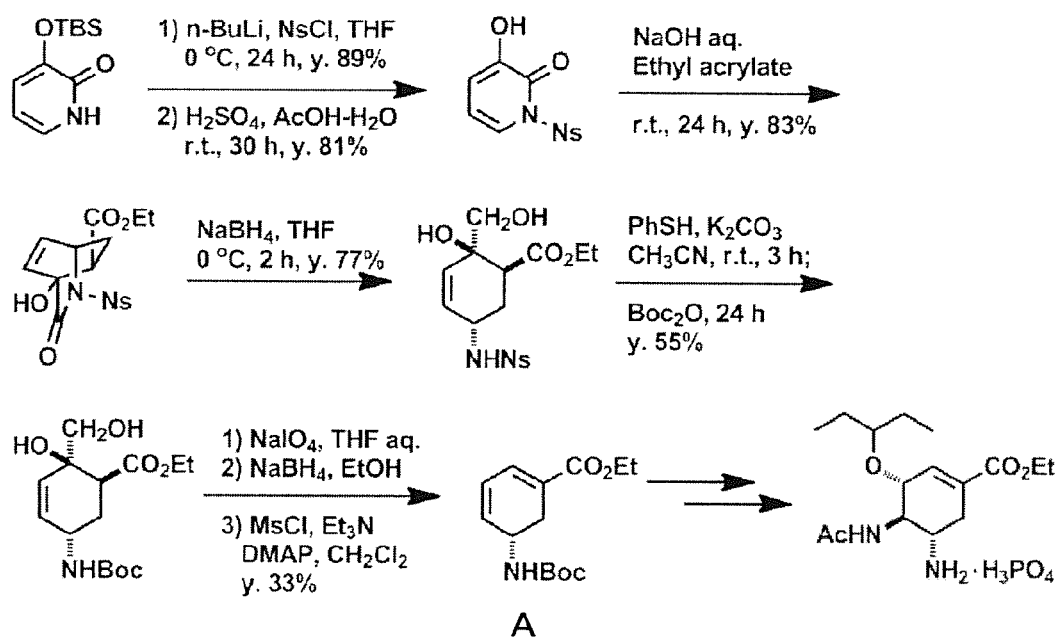
FIG. 1 is synthesis scheme showing one example of a method for synthesizing a diene compound as an intermediate leading to the synthesis of oseltamivir phosphate.

Steric configurations of chemical formulae and general formulae described herein and claims represent absolute configurations, unless particularly mentioned.

(Compound Represented by General Formula (1) and Method for Producing Same)

The compound of the present invention is a compound represented by the following general formula (1).

The method for producing the compound of the present invention is a method for producing the compound represented by the following general formula (1), the method including a reaction step of reacting together a compound represented by the following general formula (2), a compound represented by the following general formula (3), and a compound represented by the following general formula (4), and further including other steps if necessary.

<Compound Represented by General Formula (1)>

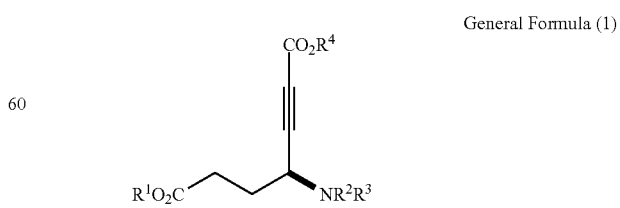

General Formula (1)

In the general formula (1), $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

The protective group of a carboxyl group in each of $R^1$ and $R^4$ is not particularly limited, can be appropriately selected depending on the purpose, and can be determined with reference to technical books such as Green et al., Protective Groups in Organic Synthesis, 3rd Edition, 1999, John Wiley & Sons, Inc.

Examples of the protective group of a carboxyl group include an alkyl group that may have a substituent, a trialkylsilyl group, and an aryl group that may have a substituent.

Examples of the alkyl group in the alkyl group that may have a substituent include an alkyl group having 1 to 6 carbon atoms. Examples of the alkyl group having 1 to 6 carbon atoms include a methyl group, an ethyl group, and a tert-butyl group. Examples of the substituent in the alkyl group that may have a substituent include a halogen atom and a phenyl group. Examples of the halogen atom include a fluorine atom, a chlorine atom, and a bromine atom. The phenyl group may further have a substituent. Examples of the substituent of the phenyl group include an alkyl group having 1 to 4 carbon atoms, a halogenated alkyl group having 1 to 4 carbon atoms, a nitro group, a halogen atom, and an alkoxy group having 1 to 4 carbon atoms.

Specific examples of the alkyl group that may have a substituent include a methyl group, an ethyl group, a tert-butyl group, and a benzyl group.

Examples of the trialkylsilyl group include a trimethylsilyl group and a triethylsilyl group.

Examples of the aryl group in the aryl group that may have a substituent include a phenyl group, a naphthalene group, and an anthracene group. Examples of the substituent in the aryl group that may have a substituent include an alkyl group having 1 to 4 carbon atoms, a halogenated alkyl group having 1 to 4 carbon atoms, a nitro group, a halogen atom, and an alkoxy group having 1 to 4 carbon atoms. Examples of the halogen atom include a fluorine atom, a chlorine atom, and a bromine atom.

Among them, an ethyl group is preferable as $R^1$ in that oseltamivir phosphate can be derived through neither removal nor exchange of the protective group, namely, ethyl ester in oseltamivir phosphate can be introduced with no need of transesterification, and thus the process for producing oseltamivir phosphate can be shortened.

Among them, as $R^4$, an alkyl group that may have a substituent is preferable, an alkyl group having 1 to 6 carbon atoms is more preferable, and a methyl group and an ethyl group are particularly preferable.

The protective group of an amino group in each of $R^2$ and $R^3$ is not particularly limited, can be appropriately selected depending on the purpose, and examples thereof include a methoxycarbonyl group, a tert-butoxycarbonyl group, a benzyloxycarbonyl group, an allyloxycarbonyl group, a formyl group, an acetyl group, a benzoyl group, a methyl group, an ethyl group, an allyl group, a benzenesulfonyl group, and a benzyl group that may have a substituent. In the case where $R^2$ and $R^3$ are taken together to form a protective group of a ring structure, examples include a phthaloyl group (Phth group).

Examples of the substituent in the benzyl group that may have a substituent include an alkyl group having 1 to 4 carbon atoms, a halogenated alkyl group having 1 to 4 carbon atoms, a nitro group, a halogen atom, and an alkoxy group having a 1 to 4 carbon atoms. Examples of the halogen atom include a fluorine atom, a chlorine atom, and a bromine atom.

Examples of the benzyl group that may have a substituent include a p-methoxybenzyl group.

Among them, an allyl group and a p-methoxybenzyl group are preferable and an allyl group is more preferable in that they can result in a high yield in the subsequent conversion and are easily deprotected.

The method for producing the compound represented by the general formula (1) is not particularly limited and can be appropriately selected depending on the purpose, but is preferably the following method for producing the compound of the present invention.

<Method for Producing Compound Represented by General Formula (1)>

The method for producing the compound of the present invention is a method for producing the compound represented by the general formula (1), the method including a reaction step of reacting together a compound represented by the following general formula (2), a compound represented by the following general formula (3), and a compound represented by the following general formula (4), and further including other steps if necessary.

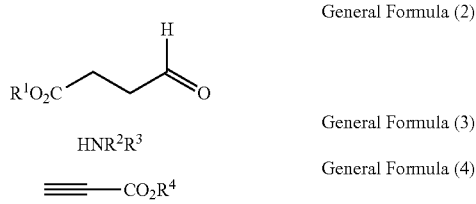

General Formula (2)

General Formula (3)

General Formula (4)

In the general formula (2), $R^1$ represents any of a protective group of a carboxyl group, and a hydrogen atom. In the general formula (3), $R^2$ and $R^3$ each independently represent any of a protective group of an amino group, and a hydrogen atom. In the general formula (4), $R^4$ represents any of a protective group of a carboxyl group, and a hydrogen atom.

$R^1$ in the general formula (2) is the same as $R^1$ in the general formula (1). Preferable aspects thereof are also the same as those of $R^1$ in the general formula (1).

$R^2$ and $R^3$ in the general formula (3) are the same as $R^2$ and $R^3$ in the general formula (1), respectively. Preferable aspects thereof are also the same as those of $R^2$ and $R^3$ in the general formula (1).

$R^4$ in the general formula (4) is the same as $R^4$ in the general formula (1). Preferable aspects thereof are also the same as those of $R^4$ in the general formula (1).

—Reaction Step—

The reaction step is not particularly limited and can be appropriately selected depending on the purpose, but is preferably performed using a catalyst.

In addition, the reaction step is preferably performed by a catalytic asymmetric reaction.

The catalyst is preferably a copper complex. As the copper complex, a copper complex of copper bromide (I) and a ligand is preferable.

The ligand is not particularly limited and can be appropriately selected depending on the purpose, and examples thereof include a pyridine bisoxazoline ligand. Examples of the pyridine bisoxazoline ligand include a compound represented by the following general formula (A).

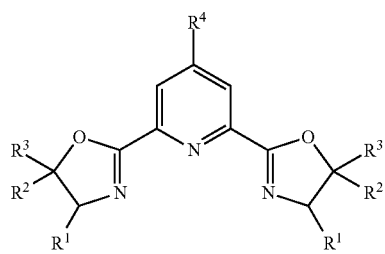

General Formula (A)

In the general formula (A), $R^1$, $R^2$, and $R^3$ each independently represent any of a hydrogen atom, an alkyl group, an alkenyl group, an aryl group, and an aralkyl group, and $R^4$ represents any of a hydrogen atom, a fluorine atom, a chlorine atom, a bromine atom, an iodine atom, an alkyl group, an alkenyl group, an aryl group, an aralkyl group, an oxygen atom, a sulfur atom, and a nitrogen atom (wherein an oxygen atom, a sulfur atom, and a nitrogen atom have any of a hydrogen atom and a substituent). It is to be noted that the alkyl group, the alkenyl group, the aryl group, and the aralkyl group may have a substituent.

The alkyl group is not particularly limited and can be appropriately selected depending on the purpose, and examples thereof include an alkyl group having 1 to carbon atoms. Examples of the alkyl group having 1 to 10 carbon atoms include a methyl group, an ethyl group, a propyl group, an i-propyl group, and a t-butyl group.

The alkenyl group is not particularly limited and can be appropriately selected depending on the purpose, and examples thereof include an alkenyl group having 2 to 10 carbon atoms. Examples of the alkenyl group having 2 to 10 carbon atoms include a vinyl group and a 1-propenyl group.

The aryl group is not particularly limited and can be appropriately selected depending on the purpose, and examples thereof include an aryl group having 4 to 14 carbon atoms in a backbone portion. Examples of the backbone portion include a phenyl group and a naphthyl group. Among them, a phenyl group is preferable as the backbone portion.

The aralkyl group (arylalkyl group) is not particularly limited, and can be appropriately selected depending on the purpose.

The compound represented by the general formula (A) is preferably (S,S)-2,6-bis(4,5-dihydro-4-phenyl-2-oxazolyl) pyridine ((S)-ph-pybox) represented by the following structure. Using such an optically-active ligand enable a catalytic asymmetric synthesis.

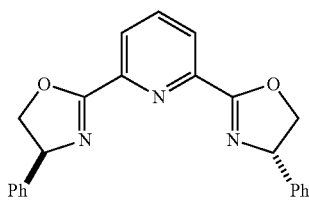

The catalyst is preferably a combination of copper bromide (I) and (S,S)-2,6-bis(4,5-dihydro-4-phenyl-2-oxazolyl)pyridine ((S)-ph-pybox) in terms of production yield and optical yield.

The amount of the catalyst to be used in the reaction step is not particularly limited and can be appropriately selected depending on the purpose, but is preferably 1% by mole to 5% by mole with respect to that of the compound represented by the general formula (2).

A solvent for use in the reaction step is not particularly limited and can be appropriately selected depending on the purpose, and examples thereof include toluene, THF (tetrahydrofuran), and ethyl acetate.

The reaction temperature in the reaction step is not particularly limited and can be appropriately selected depending on the purpose, but is preferably 0° C. to 25° C.

The reaction time in the reaction step is not particularly limited and can be appropriately selected depending on the purpose, but is preferably 3 hours to 12 hours.

The pressure in the reaction step is not particularly limited and can be appropriately selected depending on the purpose, but is preferably atmosphere pressure.

There may be a case where the compound represented by the general formula (1) of the present invention is obtained as a mixture of stereoisomers, and such a case is also encompassed within the scope of the present invention. Preferable is an optically active form (S-form excess).

The compound represented by the general formula (1) of the present invention is useful as an intermediate for industrially producing oseltamivir phosphate.

(Compound Represented by General Formula (5) and Method for Producing Same)

<Compound Represented by General Formula (5)>

The compound of the present invention is a compound represented by the following general formula (5).

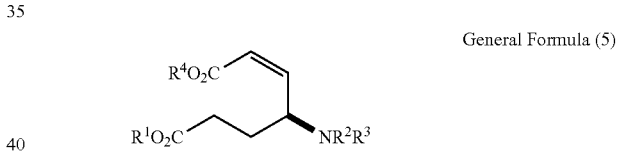

General Formula (5)

In the general formula (5), $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

Specific examples of $R^1$, $R^2$, $R^3$, and $R^4$ in the general formula (5) include those recited as the specific examples of $R^1$, $R^2$, $R^3$, and $R^4$ in the general formula (1), respectively. Preferable aspects thereof are also the same as those of $R^1$, $R^2$, $R^3$, and $R^4$ in the general formula (1), respectively.

The method for producing the compound represented by the general formula (5) is not particularly limited and can be appropriately selected depending on the purpose, but is preferably the following method for producing the compound of the present invention.

<Method for Producing Compound Represented by General Formula (5)>

The method for producing the compound of the present invention is a method for producing the compound represented by the following general formula (5), the method including a reduction step of reducing a triple bond of the compound represented by the general formula (1) to a double bond, and further including other steps if necessary.

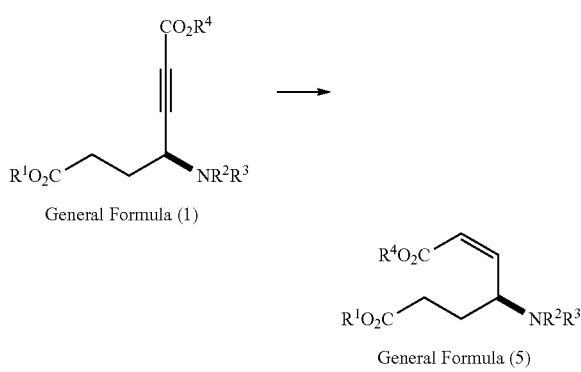

General Formula (1)

General Formula (5)

—Reduction Step—

The reduction step is not particularly limited and can be appropriately selected depending on the purpose, and examples thereof include a step of using a reducing agent.

The reducing agent is not particularly limited and can be appropriately selected depending on the purpose, but is preferably tetramethyldisiloxane.

In addition, a catalyst is preferably used in the reduction step. The catalyst is not particularly limited and can be appropriately selected depending on the purpose, but is preferably a palladium compound. Examples of the palladium compound include divalent palladium compounds such as palladium acetate and zerovalent palladium compounds such as tris(dibenzylideneacetone)dipalladium ($Pd_2(dba)_3$).

A solvent for use in the reduction step is not particularly limited and can be appropriately selected depending on the purpose, and examples thereof include toluene, THF (tetrahydrofuran), and DMF (N,N-dimethylformamide).

The reaction temperature in the reduction step is not particularly limited and can be appropriately selected depending on the purpose, but is preferably 40° C. to 60° C.

The reaction time in the reduction step is not particularly limited and can be appropriately selected depending on the purpose, but is preferably 12 hours to 24 hours.

There may be a case where the compound represented by the general formula (5) of the present invention is obtained as a mixture of stereoisomers, and such a case is also encompassed within the scope of the present invention. Preferable is an optically active form (S-form excess).

The compound represented by the general formula (5) of the present invention is useful as an intermediate for industrially producing oseltamivir phosphate.

(Compound Represented by General Formula (6) and Method for Producing Same)

<Compound Represented by General Formula (6)>

The compound of the present invention is a compound represented by the following general formula (6).

General Formula (6)

In the general formula (6), $R^1$ represents any of a protective group of a carboxyl group, and a hydrogen atom, and $R^2$ and $R^3$ each independently represent any of a protective group of an amino group, and a hydrogen atom.

It is to be noted that the compound represented by the general formula (6) is a keto-enol tautomer.

Specific examples of $R^1$, $R^2$, and $R^3$ in the general formula (6) include those recited as the specific examples of $R^1$, $R^2$, and $R^3$ in the general formula (1), respectively. Preferable aspects thereof are also the same as those of $R^1$, $R^2$, and $R^3$ in the general formula (1), respectively.

The method for producing the compound represented by the general formula (6) is not particularly limited and can be appropriately selected depending on the purpose, but is preferably the following method for producing the compound of the present invention.

<Method for Producing Compound Represented by General Formula (6)>

The method for producing the compound of the present invention is a method for producing the compound represented by the general formula (6), the method including a cyclization step of cyclizing the compound represented by the general formula (5), and further including other steps if necessary.

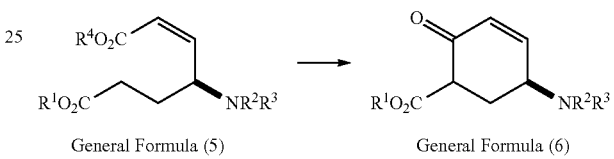

General Formula (5)    General Formula (6)

—Cyclization Step—

The cyclization step is not particularly limited, can be appropriately selected depending on the purpose, and can be performed by Dieckmann cyclization.

In the Dieckmann cyclization, a reaction can be performed under mild conditions, and lithium hexamethyldisilazide is preferably used therefor because of having a high reaction rate. For example, if potassium tert-butoxide (KOt-Bu) is used, a by-product may be produced, and if sodium hydride is used, the reaction does not progress.

A solvent for use in the cyclization step is not particularly limited and can be appropriately selected depending on the purpose, and examples thereof include toluene, THF (tetrahydrofuran), and DMF (N,N-dimethylformamide).

The reaction temperature in the cyclization step is not particularly limited and can be appropriately selected depending on the purpose, but is preferably −40° C. to −20° C.

The reaction time in the cyclization step is not particularly limited and can be appropriately selected depending on the purpose, but is preferably 30 minutes to 2 hours.

There may be a case where the compound represented by the general formula (6) of the present invention is obtained as a mixture of stereoisomers, and such a case is also encompassed within the scope of the present invention. Preferable is an optically active form (S-form excess).

The compound represented by the general formula (6) of the present invention is useful as an intermediate for industrially producing oseltamivir phosphate.

(Compound Represented by General Formula (7) and Method for Producing Same)

<Compound Represented by General Formula (7)>

The compound of the present invention is a compound represented by the following general formula (7).

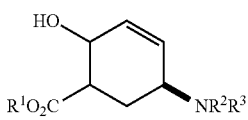

General Formula (7)

In the general formula (7), $R^1$ represents any of a protective group of a carboxyl group, and a hydrogen atom, and $R^2$ and $R^3$ each independently represent any of a protective group of an amino group, and a hydrogen atom.

Specific examples of $R^1$, $R^2$, and $R^3$ in the general formula (7) include those recited as the specific examples of $R^1$, $R^2$, and $R^3$ in the general formula (1), respectively. Preferable aspects thereof are also the same as those of $R^1$, $R^2$, and $R^3$ in the general formula (1), respectively.

The method for producing the compound represented by the general formula (7) is not particularly limited and can be appropriately selected depending on the purpose, but is preferably the following method for producing the compound of the present invention.

<Method for Producing Compound Represented by General Formula (7)>

The method for producing the compound of the present invention is a method for producing a compound represented by the general formula (7), the method including a reduction step of reducing a carbonyl group of the compound represented by the general formula (6) to a hydroxyl group, and further including other steps if necessary.

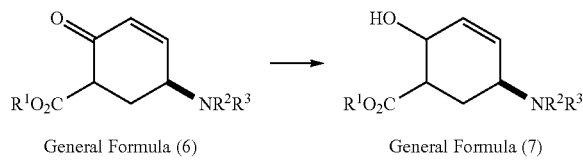

General Formula (6)  General Formula (7)

—Reduction Step—

The reduction step is not particularly limited and can be appropriately selected depending on the purpose, and examples thereof include a step of using a reducing agent such as $LiAlH_4$ or $NaBH_4$. In the case where $NaBH_4$ is used, reduction is usually performed in the presence of an alcohol such as methanol or ethanol.

A solvent for use in the reduction step is not particularly limited and can be appropriately selected depending on the purpose, and examples thereof include methanol, ethanol, toluene, THF (tetrahydrofuran), and DMF (N,N-dimethylformamide).

The reaction temperature in the reduction step is not particularly limited and can be appropriately selected depending on the purpose, but is preferably −40° C. to 0° C.

The reaction time in the reduction step is not particularly limited and can be appropriately selected depending on the purpose, but is preferably 30 minutes to 2 hours.

There may be a case where the compound represented by the general formula (7) of the present invention is obtained as a mixture of stereoisomers, and such a case is also encompassed within the scope of the present invention. Preferable is an optically active form (S-form excess).

The compound represented by the general formula (7) of the present invention is useful as an intermediate for industrially producing oseltamivir phosphate.

(Compound Represented by General Formula (8) and Method for Producing Same)

<Compound Represented by General Formula (8)>

The compound of the present invention is a compound represented by the following general formula (8).

General Formula (8)

In the general formula (8), $R^1$ represents any of a protective group of a carboxyl group, and a hydrogen atom, and $R^5$ represents any of a protective group of an amino group, and a hydrogen atom.

Specific examples of $R^1$ in the general formula (8) include those recited as the specific examples of $R^1$ in the general formula (1). Preferable aspects thereof are also the same as those of $R^1$ in the general formula (1).

The protective group of an amino group in $R^5$ in the general formula (8) is not particularly limited and can be appropriately selected depending on the purpose, and examples thereof include the protective groups of an amino group recited in the description of $R^2$ and $R^3$ in the general formula (1). Among them, a tert-butoxycarbonyl group is preferable in that the subsequent deprotection thereof is easy.

The method for producing the compound represented by the general formula (8) is not particularly limited and can be appropriately selected depending on the purpose, but is preferably the following method for producing the compound of the present invention.

<Method for Producing Compound Represented by General Formula (8)>

The method for producing the compound of the present invention is a method for producing the compound represented by the general formula (8), the method including a conversion step of converting an $NR^2R^3$ group of the compound represented by the general formula (7) to an $NHR^5$ group wherein $R^5$ is a protective group of an amino group, and the protective group $R^5$ is different from $R^2$ and $R^3$, and further including other steps if necessary.

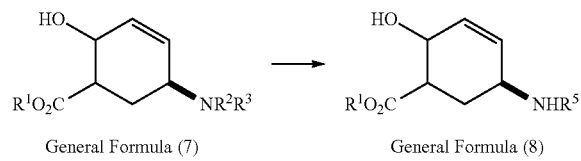

General Formula (7)  General Formula (8)

—Conversion Step—

The conversion step is not particularly limited and can be appropriately selected depending on the purpose, and examples thereof include a step of deprotecting $R^2$ and $R^3$ and then adding $R^5$ being a protective group.

A solvent for use in the conversion step is not particularly limited and can be appropriately selected depending on the purpose, and examples thereof include methylene chloride, methanol, ethanol, toluene, THF (tetrahydrofuran), and DMF (N,N-dimethylformamide).

The reaction temperature in the conversion step is not particularly limited and can be appropriately selected depending on the purpose, but is preferably 0° C. to 40° C.

The reaction time in the conversion step is not particularly limited and can be appropriately selected depending on the purpose, but is preferably 2 hours to 8 hours.

In the case where $R^2$ and $R^3$ are each an allyl group and $R^5$ is a tert-butoxycarbonyl group, for example, preferable is a step of deprotecting allyl groups of $R^2$ and $R^3$ by using tetrakis(triphenylphosphine)palladium (0) (Pd(PPh$_3$)$_4$) and N,N-dimethylbarbituric acid, and then adding a tert-butoxycarbonyl group as $R^5$ by using di-tert-butyl dicarbonate.

There may be a case where the compound represented by the general formula (8) is obtained as a mixture of stereoisomers, and such a case is also encompassed within the scope of the present invention. Herein, the compound is not a racemic form but an optically active form (S-form excess).

The compound represented by the general formula (8) of the present invention is useful as an intermediate for industrially producing oseltamivir phosphate.

(Method for Producing Compound Represented by General Formula (9))

<First Production Method>

The method for producing the compound of the present invention (first production method) is a method for producing a compound represented by the following general formula (9), the method including a dehydration step of dehydrating the compound represented by the general formula (8) by a dehydration reaction, and further including other steps if necessary.

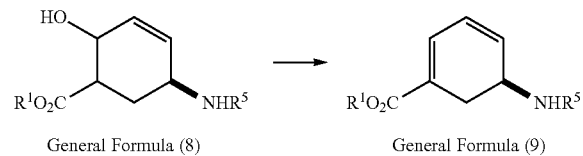

General Formula (8)      General Formula (9)

In the general formula (9), $R^1$ represents any of a protective group of a carboxyl group, and a hydrogen atom, and $R^5$ represents any of a protective group of an amino group, and a hydrogen atom.

Specific examples of $R^1$ in the general formula (9) include those recited as the specific examples of $R^1$ in the general formula (1). Preferable aspects thereof are also the same as those of $R^1$ in the general formula (1).

Specific examples of $R^5$ in the general formula (9) include those recited as the specific examples of $R^5$ in the general formula (8). Preferable aspects thereof are also the same as those of $R^5$ in the general formula (8).

The reaction temperature in the dehydration step is not particularly limited and can be appropriately selected depending on the purpose, but is preferably −20° C. to 40° C. and more preferably −2° C. to 30° C.

The reaction time in the dehydration step is not particularly limited and can be appropriately selected depending on the purpose, but is preferably 30 minutes to 5 hours and more preferably 1.5 hours to 3 hours.

In the dehydration step, a base is preferably used. The base is not particularly limited and can be appropriately selected depending on the purpose, but is preferably a diazabicyclo compound.

Examples of the diazabicyclo compound include 1,8-diazabicyclo[5.4.0]undec-7-ene (DBU), 1,5-diazabicyclo[4.3.0]nonene-5 (DBN), and 1,4-diazabicyclo[2.2.2]octane. Among them, 1,8-diazabicyclo[5.4.0]undec-7-ene is preferable in that it is inexpensively available.

In the dehydration step, the diazabicyclo compound and a tertiary amine are preferably used in combination. Using the diazabicyclo compound and the tertiary amine in combination makes it possible to provide the compound represented by the general formula (9) at a high yield.

The tertiary amine is not particularly limited and can be appropriately selected depending on the purpose, and examples thereof include trialkylamine, triallylamine, tetramethylethylenediamine, triethylenediamine, N-methylmorpholine, 4,4'-(oxydi-2,1-ethanediyl)bismorpholine, N,N-dimethylbenzylamine, pyridine, picoline, dimethylaminomethyl phenol, trisdimethylaminomethyl phenol, triethanolamine, N,N'-dimethylpiperazine, tetramethylbutanediamine, bis(2,2-morpholinoethyl)ether, and bis(dimethylaminoethyl)ether.

Examples of the trialkylamine include trimethylamine, triethylamine, tripropylamine, tributylamine, triamylamine, trihexylamine, trioctylamine, trilaurylamine, dimethylethylamine, dimethylpropylamine, dimethylbutylamine, dimethylamylamine, dimethylhexylamine, dimethylcyclohexylamine, dimethyloctylamine, and dimethyllaurylamine.

Among them, trialkylamine is preferable and triethylamine is more preferable in that they have the highest versatility and are easily available.

The amount of the diazabicyclo compound to be added in the dehydration step is not particularly limited and can be appropriately selected depending on the purpose, but is preferably 0.5 mol to 10 mol and more preferably 2 mol to 5 mol with respect to 1 mol of the compound represented by the general formula (8). If the amount to be added is less than 0.5 mol, the reaction rate may be reduced, and if it exceeds 10 mol, degradation of a substrate may occur. If the amount to be added is within the more preferable range, there is an advantage of excellent reaction rate.

The amount of the tertiary amine to be added in the dehydration step is not particularly limited and can be appropriately selected depending on the purpose, but is preferably 0.5 mol to 10 mol and more preferably 2 mol to 5 mol with respect to 1 mol of the compound represented by the general formula (8). If the amount to be added is less than 0.5 mol, the reaction rate may be reduced, and if it exceeds 10 mol, a by-product may be generated. If the amount to be added is within the more preferable range, there is an advantage of excellent reaction rate.

<Second Production Method>

The method for producing the compound of the present invention (second production method) is a method for producing the compound represented by the general formula (9), the method including:

reacting together the compound represented by the general formula (2), the compound represented by the general formula (3), and the compound represented by the general formula (4) to provide the compound represented by the general formula (1);

reducing a triple bond of the compound represented by the general formula (1) to a double bond to provide the compound represented by the general formula (5);

cyclizing the compound represented by the general formula (5) to provide the compound represented by the general formula (6);

reducing a carbonyl group of the compound represented by the general formula (6) to a hydroxyl group to provide the compound represented by the general formula (7);

converting an NR$^2$R$^3$ group of the compound represented by the general formula (7) to an NHR$^5$ group, wherein R$^5$ is a protective group of an amino group and the protective group R$^5$ is different from R$^2$ and R$^3$, to provide the compound represented by the general formula (8); and dehydrating the compound represented by the general formula (8) by a dehydration reaction to provide the compound represented by the general formula (9); and further including other steps if necessary.

The respective steps in the production method are the same as the respective steps in the production method of the present invention described above.

That is, the step of providing the compound represented by the general formula (1) is the same as the step described in the method for producing the compound represented by the general formula (1) of the present invention. Preferable aspects thereof are also ditto.

The step of providing the compound represented by the general formula (5) is the same as the reduction step in the method for producing the compound represented by the general formula (5) of the present invention. Preferable aspects thereof are also ditto.

The step of providing the compound represented by the general formula (6) is the same as the cyclization step in the method for producing the compound represented by the general formula (6) of the present invention. Preferable aspects thereof are also ditto.

The step of providing the compound represented by the general formula (7) is the same as the reduction step in the method for producing the compound represented by the general formula (7) of the present invention. Preferable aspects thereof are also ditto.

The step of providing the compound represented by the general formula (8) is the same as the conversion step in the method for producing the compound represented by the general formula (8) of the present invention. Preferable aspects thereof are also ditto.

The step of providing the compound represented by the general formula (9) is the same as the dehydration step in the method for producing the compound represented by the general formula (9) of the present invention (first production method). Preferable aspects thereof are also ditto.

(Method for Producing Oseltamivir Phosphate)

The method for producing oseltamivir phosphate of the present invention includes: the method for producing the compound represented by the general formula (1), the method for producing the compound represented by the general formula (5), the method for producing the compound represented by the general formula (6), the method for producing the compound represented by the general formula (7), the method for producing the compound represented by the general formula (8), or the method for producing the compound represented by the general formula (9), or any combination thereof; and further includes other steps if necessary.

The oseltamivir phosphate is known as a trade name "Tamiflu," and is a compound represented by the following structure.

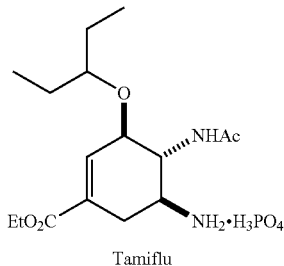

Tamiflu

<Other Steps>

The aforementioned other steps include a step of using the compound represented by the general formula (9) to synthesize the oseltamivir phosphate. Such a step is not particularly limited and can be appropriately selected depending on the purpose, and examples thereof include a step described in J. Am. Chem. Soc., 128, 6310, 2006. One example of this step includes a step represented by the following synthesis scheme.

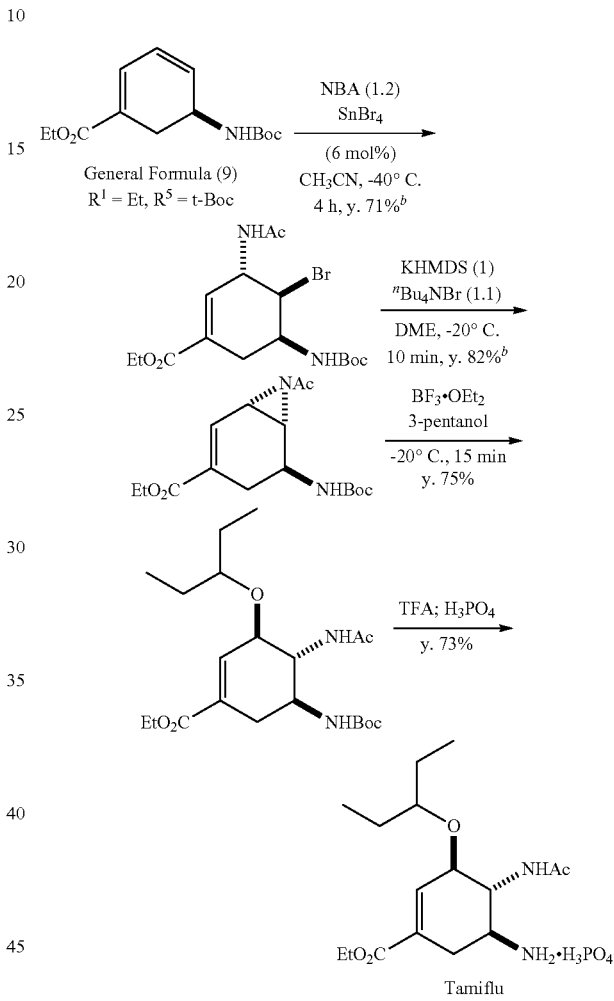

b) J. Am. Chem. Soc. 2006, 128, 63

In the synthesis scheme, "Et" represents an "ethyl group." "Boc" and "t-Boc" represent a "tert-butoxycarbonyl group." "NBA" represents "N-bromoacetamide." "Ac" represents an "acetyl group." "KHMDS" represents "potassium hexamethyldisilazide." "$^n$Bu" represents a "n-butyl group." "DME" represents "dimethoxyethane." "TFA" represents "trifluoroacetic acid." The numeral values in parentheses of "NBA," "KHMDS," and "$^n$Bu$_4$NBr" represent an amount in equivalents.

It is to be noted that the reaction conditions and reagents shown in the synthesis scheme are examples, and the reaction in the step are not limited by these specific conditions and reagents.

EXAMPLES

Hereinafter, the present invention will be specifically described with reference to Examples, but the present invention is not limited to these Examples at all.

In Examples, "Me"" represents a "methyl group." "Et" represents an "ethyl group." "Boc" represents a "tert-butoxycarbonyl group."

Example 1

Synthesis of Compound 1-1

Monovalent copper bromide (available from Wako Chemical, Ltd., 2.9 mg, 0.0200 mmol, 5% by mole) and the following ligand A-1 (available from Sigma-Aldrich Co. LLC, 8.1 mg, 0.0220 mmol, 5.5% by mole) were charged to a well-dried test tube, and toluene (1.6 mL) was added thereto under stirring at room temperature. After stirring at room temperature for 30 minutes, a molecular sieve 4A (MS4A, 240 mg), the following compound 4-1 (available from Wako Chemical, Ltd., 0.0811 mL, 0.800 mmol, 2 equivalents), the following compound 2-1 (0.0500 mL, 0.400 mmol, 1 equivalent, synthesized according to Coffin, B.; Robbins, R. F. J. Chem. Soc. C 1996, 334.), and the following compound 3-1 (available from Tokyo Chemical Industry Co., Ltd., 0.0988 mL, 0.800 mmol, 2 equivalents) were sequentially added thereto, and stirred at room temperature for 14 hours. Subsequently, the resultant was subjected to filtration and concentration, and also to silica gel purification (hexane/ethyl acetate=8/1 to 6/1 (volume ratio)), thereby providing the following compound 1-1 (109.9 mg, 0.358 mmol, yield: 89%, 43% e.e.).

The Rf (Relative to Front) value, $^1$H NMR spectrum, $^{13}$C NMR spectrum, IR spectrum, ESI-MS spectrum, ESI-HRMS spectrum, specific optical rotation, and HPLC data of the obtained compound 1-1 are shown below.

Rf value: 0.3 (hexane/ethyl acetate=6/1 (volume ratio))
$^1$H NMR (CDCl$_3$, 400 MHz): δ 5.73 (m, 2H), 5.21 (d, J=17.0 Hz, 2H), 5.11 (d, J=10.5 Hz, 2H), 4.21 (q, J=7.1 Hz, 2H), 4.11 (q, J=7.0 Hz, 2H), 3.71 (dd, J=7.8 Hz, 7.1 Hz, 1H), 3.28 (m, 2H), 2.87 (dd, J=14.0 Hz, 7.8 Hz, 2H), 2.42 (m, 2H), 1.99 (m, 2H), 1.30 (t, J=7.1 Hz, 3H), 1.24 (t, J=7.0 Hz, 3H)
$^{13}$C NMR (CDCl$_3$, 100 MHz) δ 172.9, 153.6, 135.9, 117.7, 85.9, 77.6, 62.0, 60.5, 53.7, 51.3, 30.9, 27.9, 14.3, 14.0
IR (neat, cm$^{-1}$) 3081, 2981, 2819, 2225, 1740, 1712
ESI-MS m/z 330.2 [M+Na]$^+$
ESI-HRMS Calcd for C$_{17}$H$_{25}$NO$_4$Na [M+Na]$^+$: 330.1676. Found: 330.1674.
[α]$_D^{22}$=−40.1 (34% ee, c=0.97, CHCl$_3$)
HPLC (hexane/isopropanol=50/1 (volume ratio), CHIRALPAK IC, 0.5 mL/min, 254 nm) t$_R$=17.8 min (minor), 19.6 min (major).

Example 2

Synthesis of Compound 1-2

The same synthesis procedure as in Example 1 was performed except that the compound 3-1 in Example 1 was replaced to the following compound 3-2 (synthesized according to Anastasi, C.; Hantz, O.; Clercq, E. D.; Pannecouque, C.; Clayette, P.; Dereuddre-Bosquet, N.; Dormont, D.; Gondois-Rey, F.; Hirsch, I.; Kraus, J.-L. J. Med. Chem. 2004, 47, 1183.), thereby providing the following compound 1-2 (yield: 83%, 25% e.e.).

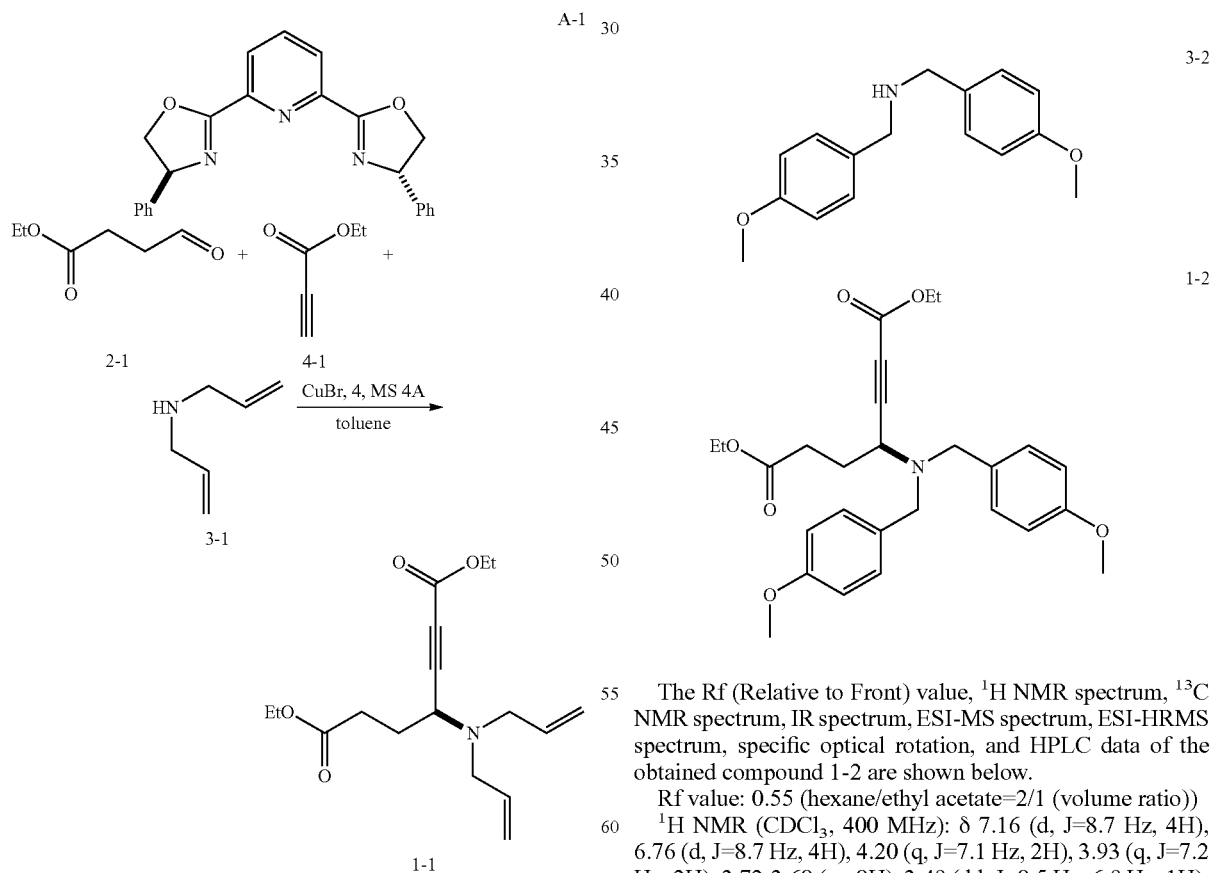

The Rf (Relative to Front) value, $^1$H NMR spectrum, $^{13}$C NMR spectrum, IR spectrum, ESI-MS spectrum, ESI-HRMS spectrum, specific optical rotation, and HPLC data of the obtained compound 1-2 are shown below.

Rf value: 0.55 (hexane/ethyl acetate=2/1 (volume ratio))
$^1$H NMR (CDCl$_3$, 400 MHz): δ 7.16 (d, J=8.7 Hz, 4H), 6.76 (d, J=8.7 Hz, 4H), 4.20 (q, J=7.1 Hz, 2H), 3.93 (q, J=7.2 Hz, 2H), 3.72-3.68 (m, 8H), 3.49 (dd, J=8.5 Hz, 6.9 Hz, 1H), 3.23 (d, J=13.3 Hz, 2H), 2.37-2.23 (m, 2H), 1.97-1.93 (m, 2H), 1.27 (t, J=7.1 Hz, 3H), 1.10 (t, J=7.2 Hz, 3H)
$^{13}$C NMR (CDCl$_3$, 100 MHz): δ 172.7, 158.9, 153.7, 130.8, 130.0, 113.8, 85.8, 77.8, 62.1, 60.5, 55.3, 54.1, 50.6, 30.8, 27.7, 14.2, 14.2

IR (neat, cm$^{-2}$) 2981, 2834, 2221, 1731, 1712
ESI-MS m/z 490.2 [M+Na]$^+$
ESI-HRMS Calcd for $C_{21}H_{33}NO_6Na$ [M+Na]$^+$: 490.2200. Found: 490.2197.
$[\alpha]_D23=-37.9$ (25% ee, c=1.05, $CHCl_3$)
HPLC (hexane/isopropanol=50/1 (volume ratio), CHIRALPAK IC, 1.0 mL/min, 254 nm) $t_R$=39.7 min (minor), 50.0 min (major).

Example 3

Synthesis of Compound 1-3

The same synthesis procedure as in Example 1 was performed except that the compound 3-1 in Example 1 was replaced to the following compound 3-3 (synthesized according to Lee, O.-Y.; Law, K.-L.; Yang, D. Org. Lett. 2009, 11, 3302), thereby providing the following compound 1-3 (yield: 82%, 35% e.e.).

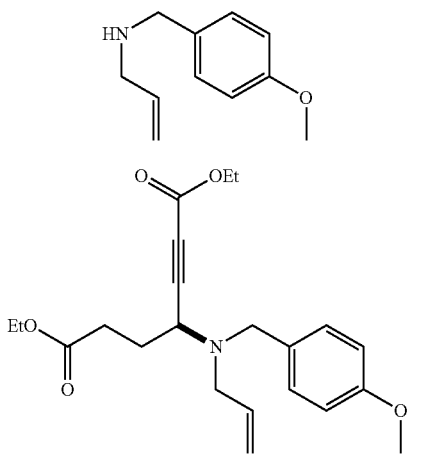

The Rf (Relative to Front) value, $^1$H NMR spectrum, $^{13}$C NMR spectrum, IR spectrum, ESI-MS spectrum, ESI-HRMS spectrum, specific optical rotation, and HPLC data of the obtained compound 1-3 are shown below.

Rf value: 0.5 (hexane/ethyl acetate=4/1 (volume ratio))

$^1$H NMR ($CDCl_3$, 400 MHz): δ 7.25 (d, J=8.7 Hz, 2H), 6.86 (d, J=8.7 Hz, 2H), 5.79 (m, 1H), 5.28 (d, J=17.2 Hz, 1H), 5.16 (d, J=10.1 Hz, 1H), 4.28 (q, J=7.1 Hz, 2H), 4.11 (q, J=7.1 Hz, 2H), 3.85 (d, J=13.5 Hz, 1H), 3.81 (s, 3H), 3.66 (dd, J=8.5 Hz, 7.1 Hz, 1H), 3.33-3.28 (m, 2H), 2.94 (dd, J=14.4, 8.2 Hz, 1H), 2.42 (m, 2H), 2.02 (m, 2H), 1.36 (t, J=7.1 Hz, 3H), 1.26 (t, J=7.1 Hz, 3H)

$^{13}$C NMR ($CDCl_3$, 100 MHz): δ 172.8, 158.8, 153.6, 136.0, 130.8, 130.0, 117.8, 113.8, 85.9, 77.7, 62.1, 60.5, 55.3, 54.3, 53.5, 51.0, 30.8, 27.8, 14.3, 14.1

IR (neat, cm$^{-1}$) 2981, 2834, 2221, 1731, 1712
ESI-MS m/z 410.3 [M+Na]$^+$
ESI-HRMS Calcd for $C_{22}H_{29}NO_5Na$ [M+Na]$^+$: 410.1938. Found: 410.1935.
$[\alpha]_D^{22}=-58.0$ (35% ee, c=0.95, $CHCl_3$)
HPLC (hexane/isopropanol=50/1 (volume ratio), CHIRALPAK IC, 1.0 mL/min, 254 nm) $t_R$=16.9 min (minor), 19.3 min (major).

Example 4

Synthesis of Compound 1-4

The same synthesis procedure as in Example 1 was performed except that the compound 4-1 in Example 1 was replaced to the following compound 4-4 (available from Wako Chemical, Ltd.), thereby providing the following compound 1-4 (yield: 89%, 41% e.e.).

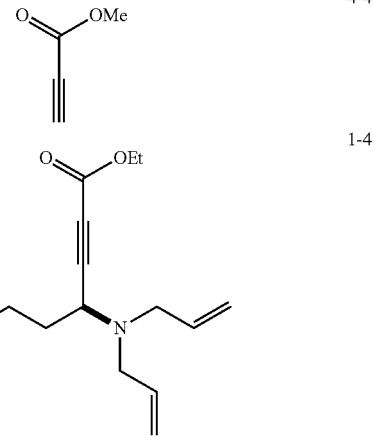

The Rf (Relative to Front) value, $^1$H NMR spectrum, $^{13}$C NMR spectrum, IR spectrum, ESI-MS spectrum, ESI-HRMS spectrum, specific optical rotation, and HPLC data of the obtained compound 1-4 are shown below.

Rf value: 0.3 (hexane/ethyl acetate=6/1 (volume ratio))

$^1$H NMR ($CDCl_3$, 400 MHz): δ 5.72 (m, 2H), 5.20 (d, J=17.0 Hz, 2H), 5.11 (d, J=10.5 Hz, 2H), 4.12 (q, J=7.0 Hz, 2H), 3.70 (m, 4H), 3.27 (m, 2H), 2.87 (dd, J=14.0 Hz, 7.8 Hz, 2H), 2.41 (m, 2H), 2.00 (m, 2H), 1.24 (t, J=7.0 Hz, 3H)

$^{13}$C NMR ($CDCl_3$, 100 MHz): δ 172.6, 153.8, 135.9, 117.6, 85.7, 77.6, 60.5, 53.5, 52.5, 51.5, 30.9, 28.0, 14.0

IR (neat, cm$^{-1}$) 3080, 2980, 2819, 2222, 1742, 1713
ESI-MS m/z 316.2 [M+Na]$^+$
ESI-HRMS Calcd for $C_{16}H_{23}NO_4Na$ [M+Na]$^+$: 316.1519. Found: 316.1518.
$[\alpha]_D^{23}=-52.3$ (41% ee, c=0.98, $CHCl_3$)
HPLC (hexane/isopropanol=50/1 (volume ratio), CHIRALPAK IC, 0.5 mL/min, 254 nm) $t_R$=18.2 min (minor), 20.1 min (major).

Example 5

Synthesis of Compound 5-1

To $Pd_2(dba)_3 \cdot CHCl_3$ (available from Sigma-Aldrich Co. LLC, chloroform adduct of tris(dibenzylideneacetone)dipalladium (0), 105 mg, 0.102 mmol, 2.5% by mole) and tris(2-methylphenyl)phosphine (available from Tokyo Chemical Industry Co., Ltd., P (o-tol)$_3$, 124 mg, 0.406 mmol, 10% by mole) dissolved in toluene (10.3 mL) were sequentially added 1,1,3,3-tetramethyldisiloxane (available from Tokyo Chemical Industry Co., Ltd., $Me_2HSiOSiHMe_2$, 0.718 mL, 4.06 mmol, 1 equivalent), acetic acid (AcOH, 0.232 mL, 4.06 mmol, 1 equivalent), and a solution of the compound 1-1 synthesized in Example 1 in toluene (0.406 M, 10 mL, 4.06 mmol, 1 equivalent) at room temperature, and stirred at 45° C. for 19 hours. After the resultant was cooled to room temperature, ethyl acetate and an aqueous saturated sodium hydrogen carbonate solution were added thereto. The aqueous layer was extracted with ethyl acetate, and the organic layer was washed with saturated saline and then dried with sodium sulfate, and then subjected to distillation off of the solvent and silica gel purification (hexane/ethyl acetate=9/1 to 7/1 (volume ratio)), thereby providing the following compound 5-1 (450 mg, 1.45 mmol) at a yield of 36%.

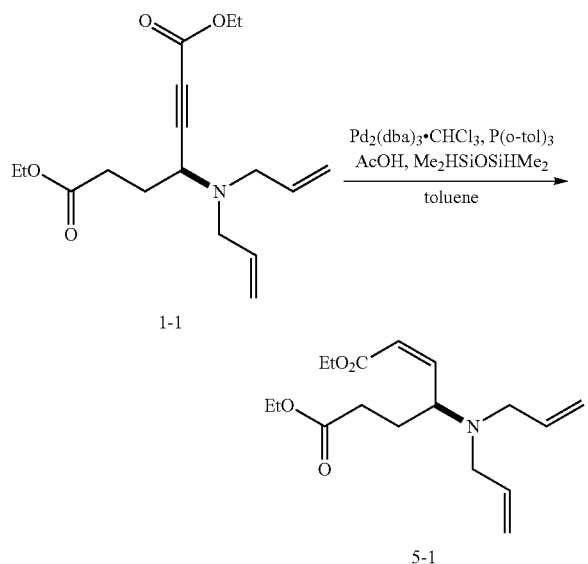

The Rf (Relative to Front) value, $^1$H NMR spectrum, $^{13}$C NMR spectrum, IR spectrum, ESI-MS spectrum, ESI-HRMS spectrum, and specific optical rotation of the obtained compound 5-1 are shown below.

Rf value: 0.3 (hexane/ethyl acetate=4/1 (volume ratio))

$^1$H NMR(CDCl$_3$, 400 MHz): δ 6.12 (dd, J=11.4 Hz, 10.3 Hz, 1H), 5.89 (d, J=11.4 Hz, 1H), 5.80-5.70 (m, 2H), 5.13-5.04 (m, 4H), 4.45 (m, 1H), 4.15-4.07 (m, 4H), 3.26 (m, 2H), 2.91 (dd, J=14.4 Hz, 7.4 Hz, 2H), 2.46 (m, 1H), 2.30 (m, 1H), 1.93 (m, 1H), 1.73 (m, 1H), 1.28-1.21 (m, 6H)

$^{13}$C NMR (CDCl$_3$, 100 MHz): δ 173.7, 165.8, 147.4, 136.6, 122.1, 116.7, 60.2, 60.2, 56.1, 52.6, 31.1, 27.4, 14.3, 14.3

IR (neat, cm$^{-1}$) 3077, 2981, 2811, 1720

ESI-MS m/z 332.2 [M+Na]$^+$

ESI-HRMS Calcd for C$_{17}$H$_{25}$NO$_4$ [M+H]$^+$: 310.2013. Found: 310.2010.

[α]$_D^{22}$=44.2 (34% ee, c=0.90, CHCl$_3$).

Example 6

Synthesis of Compound 6-1

The compound 5-1 obtained in Example 5 (340 mg, 1.10 mmol) was dissolved in THF (tetrahydrofuran, 5.49 mL), and a solution of lithium hexamethyldisilazide
(LHMDS) in THF (1.0 M, 3.30 mL, 3.30 mmol, 3 equivalents) was slowly added thereto at −40° C. and stirred for 30 minutes. After the resultant was diluted with ethyl acetate, an aqueous saturated ammonium chloride solution was added thereto, and the aqueous layer was extracted with ethyl acetate. The organic layer was washed with saturated saline and dried with sodium sulfate, and then the solvent was distilled off, thereby providing the following compound 6-1 (314 mg) as a keto-enol mixture. The obtained crude product was used in the next reaction as it was.

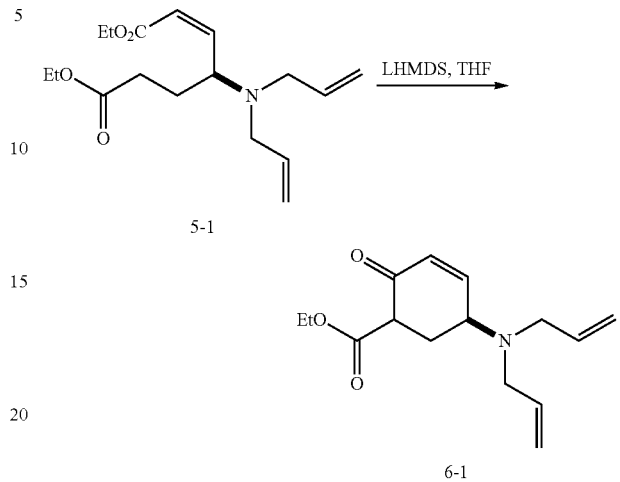

The Rf (Relative to Front) value, IR spectrum, ESI-MS spectrum, and ESI-HRMS spectrum of the obtained compound 6-1 are shown below.

Rf value: 0.2 (hexane/ethyl acetate=4/1 (volume ratio))

IR (neat, cm$^{-1}$) 2981, 2815, 1739, 1685

ESI-MS m/z 286.1 [M+Na]$^+$ ESI-HRMS Calcd for C$_{15}$H$_{22}$NO$_3$ [M+H]$^+$: 264.1594. Found: 264.1592.

Figure 2:
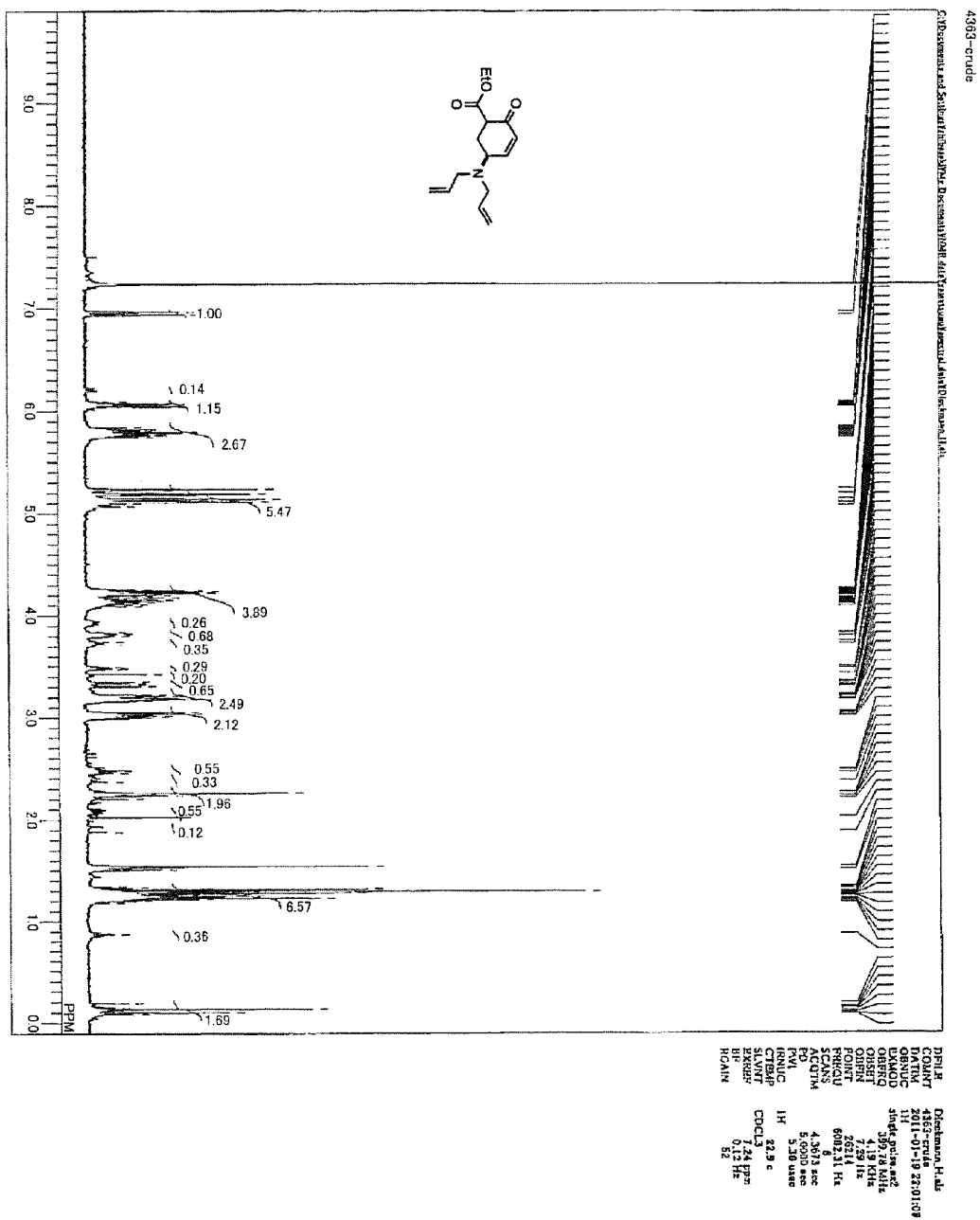
FIG. 2 is the $^1$H NMR spectrum of a compound 6-1 in Example 6.

The $^1$H NMR spectrum is shown in FIG. 2.

Example 7

Synthesis of Compound 7-1

The compound 6-1 obtained in Example 6 (crude product, 312 mg) was dissolved in methanol (MeOH, 5.49 mL), and sodium borohydride (NaBH$_4$, 83.2 mg, 2.20 mmol) was added thereto at −20° C. and stirred for 30 minutes. An aqueous saturated ammonium chloride solution was added thereto, and thereafter, methanol was distilled off under reduced pressure. Ethyl acetate was further added thereto, and the produced aqueous layer was extracted with ethyl acetate. The organic layer was washed with saturated saline and dried with sodium sulfate, and then subjected to distillation off of the solvent and silica gel purification (hexane/ethyl acetate=2/1 (volume ratio)), thereby providing the following compound 7-1 (180 mg, 0.680 mmol) as a diastereomer mixture at a yield of 62%.

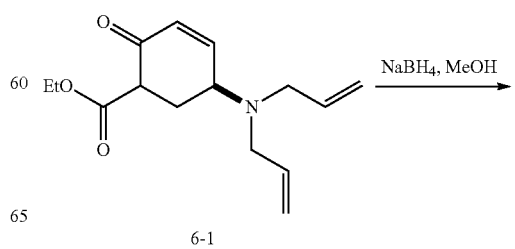

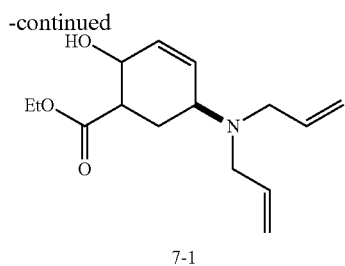

7-1

The Rf (Relative to Front) value, IR spectrum, ESI-MS spectrum, and ESI-HRMS spectrum of the obtained compound 7-1 are shown below.

Figure 3:
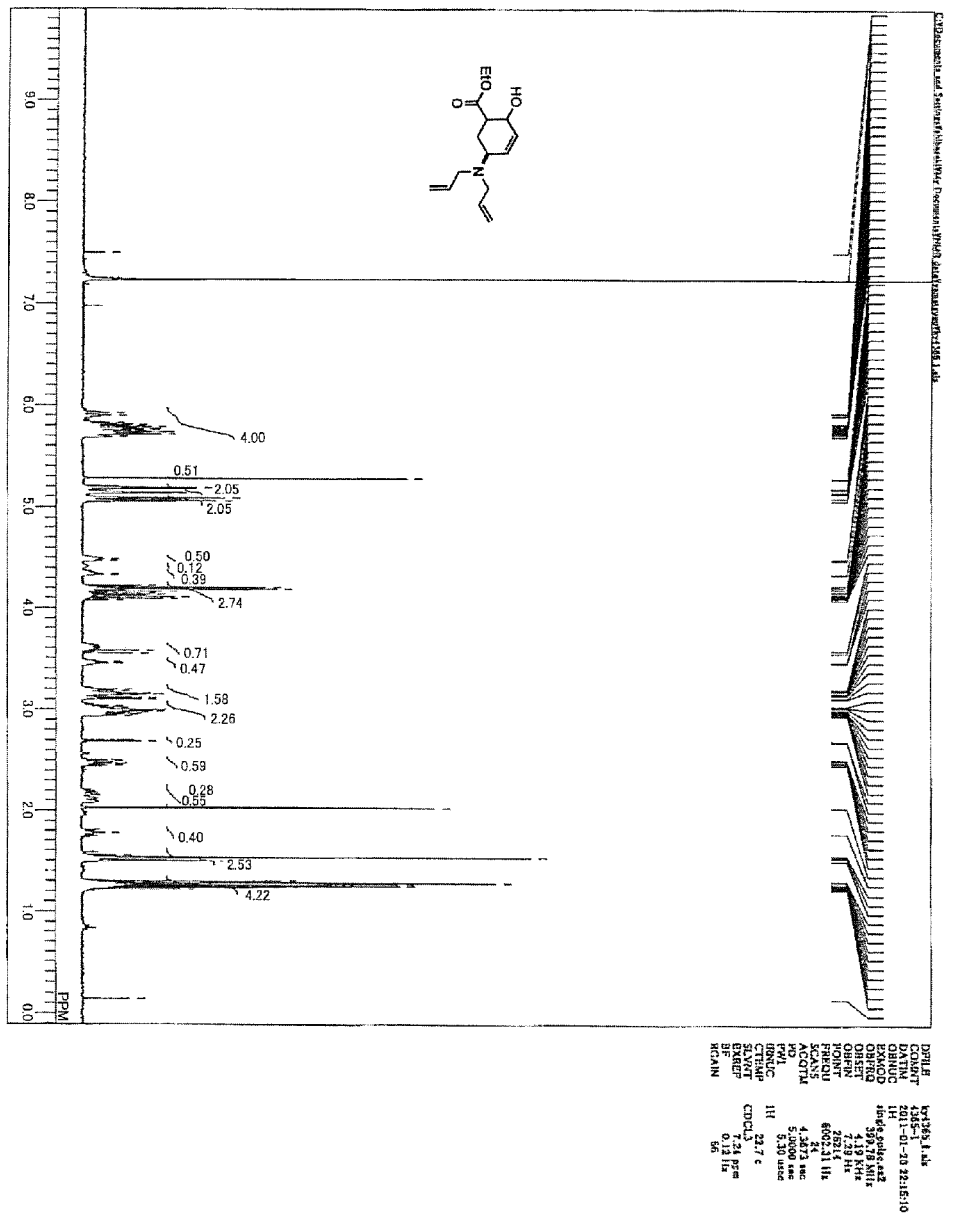
FIG. 3 is the $^1$H NMR spectrum of a compound 7-1 in Example 7.

Rf value: 0.1 (hexane/ethyl acetate=4/1 (volume ratio))
IR (neat, cm$^{-1}$) 2978, 2811, 1731
ESI-MS m/z 288.2 [M+Na]$^+$
ESI-HRMS Calcd for $C_{15}H_{21}NO_3$ [M+H]$^+$: 266.1751. Found: 266.1750.
The $^1$H NMR spectrum is shown in FIG. 3.

Example 8

Synthesis of Compound 8-1

The compound 7-1 synthesized in Example 7 (180 mg, 0.680 mmol) was dissolved in methylene chloride (3.39 mL), and Pd(PPh$_3$)$_4$ (available from Tokyo Chemical Industry Co., Ltd., tetrakis(triphenylphosphine)palladium (0), 78.4 mg, 0.0678 mmol, 10% by mole) and N,N-dimethylbarbituric acid (636 mg, 4.07 mmol, 6 equivalents) were sequentially added thereto at room temperature and then stirred for 1 hour. The solvent was distilled off, and a solution of Boc$_2$O (di-tert-butyl dicarbonate) in acetonitrile (0.82 M, 4.13 mL, 3.39 mmol, 5 equivalents) and an aqueous saturated sodium hydrogen carbonate solution (3.39 mL) were sequentially added thereto and stirred at room temperature for 3 hours. After the resultant was diluted with ethyl acetate, an aqueous saturated sodium hydrogen carbonate solution was added thereto and the aqueous layer was extracted with ethyl acetate. The organic layer was washed with saturated saline, dried with sodium sulfate, and then subjected to distillation off of the solvent and silica gel purification (hexane/ethyl acetate=1/1 (volume ratio)), thereby providing the following compound 8-1 (175 mg, 0.613 mmol) as a diastereomer mixture at a yield of 91%.

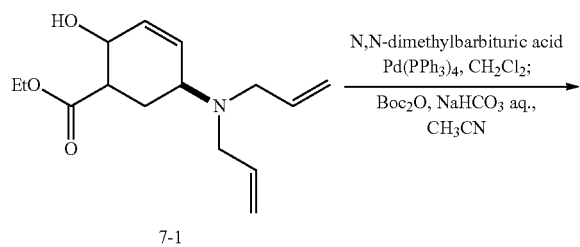

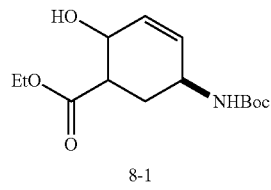

8-1

The Rf (Relative to Front) value, IR epectrum, ESI-MS spectrum, and ESI-HRMS spectrum of the obtained compound 8-1 are shown below.

Figure 4:
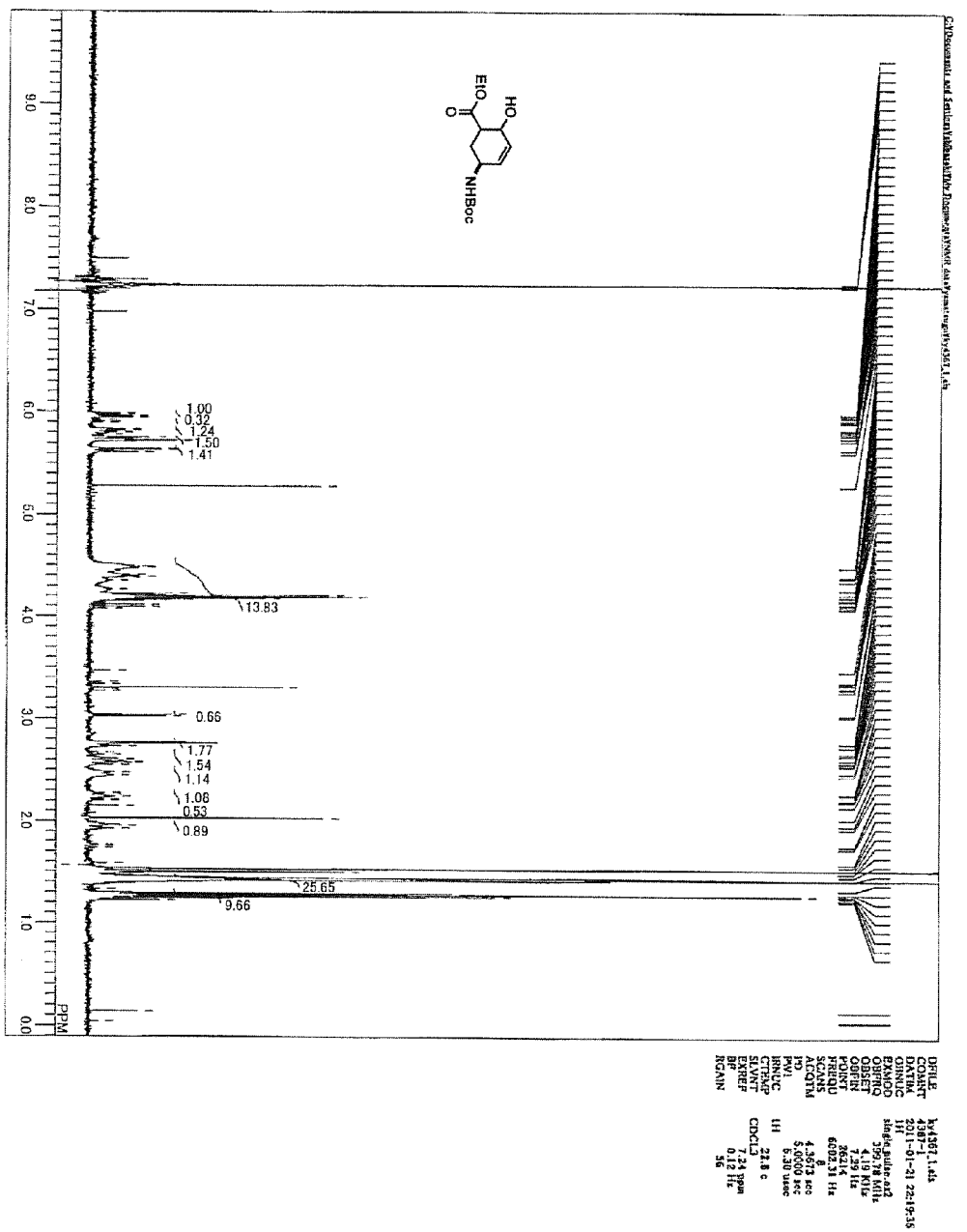
FIG. 4 is the $^1$H NMR spectrum of a compound 8-1 in Example 8.

Rf value: 0.15 (hexane/ethyl acetate=2/1 (volume ratio))
IR (neat, cm$^{-1}$) 3367, 2977, 1689
ESI-MS m/z 308.1 [M+Na]$^+$
ESI-HRMS Calcd for $C_{14}H_{23}NO_5Na$ [M+Na]$^+$: 308.1468. Found: 308.1468.
The $^1$H NMR spectrum is shown in FIG. 4.

The result that the compound 9-1 obtained in Example 9 hereafter is an optically active form of the S-form excess confirms that the obtained compound 8-1 is also an optically active form of the S-form excess.

Example 9

Synthesis of Compound 9-1

The compound 8-1 obtained in Example 8 (172 mg, 0.603 mmol) was dissolved in methylene chloride (3.01 mL), methanesulfonyl chloride (0.0513 mL, 0.663 mmol, 1.1 equivalents) and triethylamine (0.167 mL, 1.21 mmol, 2 equivalents) were sequentially added thereto under cooling in ice and stirred for 10 minutes, and thereafter 1,8-diazabicyclo[5.4.0]undec-7-ene (DBU, 0.279 mL, 1.87 mmol, 3.1 equivalents) was further added thereto and stirred at 25° C. for 1 hour. After the resultant was diluted with methylene chloride and water, the aqueous layer was extracted with methylene chloride. The organic layer was sequentially washed with an aqueous 1 N hydrochloric acid solution, an aqueous saturated sodium hydrogen carbonate solution and saturated saline, dried with sodium sulfate, and then subjected to distillation off of the solvent and silica gel purification (hexane/diethyl ether=3/1 to 2/1 (volume ratio)), thereby providing the following compound 9-1 (140 mg, 0.523 mmol) at a yield of 87%.

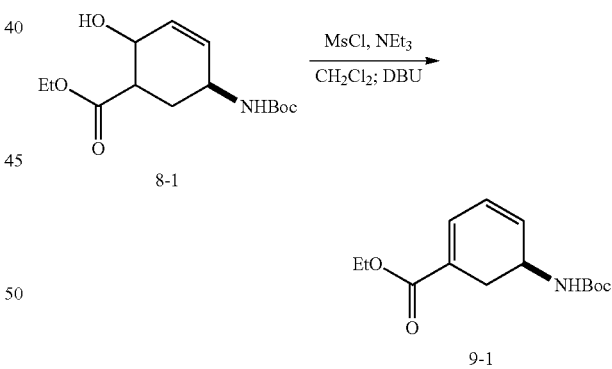

9-1

The Rf (Relative to Front) value, $^1$H NMR spectrum, $^{13}$C NMR spectrum, IR spectrum, ESI-MS spectrum, ESI-HRMS spectrum, and specific optical rotation of the obtained compound 9-1 are shown below.

Rf value: 0.3 (hexane/ethyl acetate=4/1 (volume ratio))
$^1$H NMR (CDCl$_3$, 400 MHz): δ 7.03 (d, J=3.9 Hz, 1H), 6.18-6.09 (m, 2H), 4.61 (m, 1H), 4.42 (m, 1H), 4.20 (q, J=7.1 Hz, 2H), 2.76-2.61 (m, 2H), 1.42 (s, 9H), 1.29 (t, J=7.1 Hz, 3H)
$^{13}$C NMR (CDCl$_3$, 100 MHz): δ 166.8, 154.9, 132.7, 131.7, 127.0, 124.8, 79.5, 60.6, 43.5, 28.8, 28.4, 14.3
IR (neat, cm$^1$) 3352, 2978, 1705
ESI-MS m/z 290.1 [M+Na]$^+$ ESI-HRMS Calcd for $C_{14}H_{21}NO_4Na$ $[M+Na]^+$: 290.1363. Found: 290.1361.

$[\alpha]_D^{23} = -80.5$ (34% ee, c=1.00, $CHCl_3$), lit.$[\alpha]_D^{20} = -217$ (>99% ee, c=1.1, $CHCl_3$) (Bromfield, K. M.; Graden, H.; Hagberg, D. P.; Olsson, T.; Kann, N. Chem. Commun. 2007, 3183.)

INDUSTRIAL APPLICABILITY

The compounds of the present invention are intermediates useful for industrially producing oseltamivir phosphate, and thus can be suitably used for producing oseltamivir phosphate.

The methods for producing the compound of the present invention can produce intermediates useful for industrially producing oseltamivir phosphate.

The method for producing oseltamivir phosphate of the present invention is a production method suitable for industrial production, and can be suitably used for industrially producing oseltamivir phosphate.

Aspects of the present invention are, for example, the following.

<1> A compound represented by the following general formula (1):

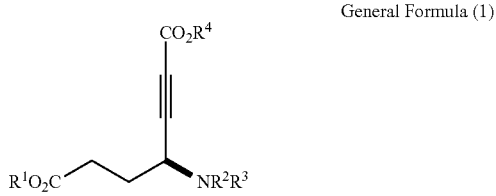

General Formula (1)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

<2> A compound represented by the following general formula (5):

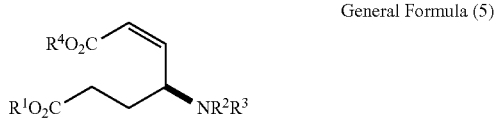

General Formula (5)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

<3> A compound represented by the following general formula (6):

General Formula (6)

wherein $R^1$ represents any of a protective group of a carboxyl group, and a hydrogen atom, and $R^2$ and $R^3$ each independently represent any of a protective group of an amino group, and a hydrogen atom.

<4> A compound represented by the following general formula (7):

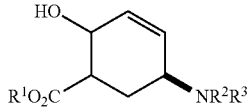

General Formula (7)

wherein $R^1$ represents any of a protective group of a carboxyl group, and a hydrogen atom, and $R^2$ and $R^3$ each independently represent any of a protective group of an amino group, and a hydrogen atom.

<5> A compound represented by the following general formula (8):

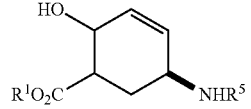

General Formula (8)

wherein $R^1$ represents any of a protective group of a carboxyl group, and a hydrogen atom, and $R^5$ represents any of a protective group of an amino group, and a hydrogen atom.

<6> A method for producing the compound represented by the general formula (1) according to <1>, the method including:

reacting together a compound represented by the following general formula (2), a compound represented by the following general formula (3), and a compound represented by the following general formula (4):

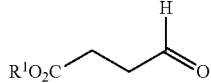

General Formula (2)

General Formula (3)

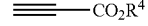

General Formula (4)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

<7> A method for producing the compound represented by the general formula (5) according to <2>, the method including:

reducing a triple bond of the compound represented by the general formula (1) according to <1> to a double bond.

<8> A method for producing the compound represented by the general formula (6) according to <3>, the method including:

cyclizing the compound represented by the general formula (5) according to <2>.

<9> A method for producing the compound represented by the general formula (7) according to <4>, the method including:

reducing a carbonyl group of the compound represented by the general formula (6) according to <3> to a hydroxyl group.

<10> A method for producing the compound represented by the general formula (8) according to <5>, the method including:

converting an $NR^2R^3$ group of the compound represented by the general formula (7) according to <4> to an $NHR^5$ group wherein $R^5$ is a protective group of an amino group, and the protective group $R^5$ is different from $R^2$ and $R^3$.

<11> A method for producing a compound represented by the following general formula (9), the method including:

dehydrating the compound represented by the general formula (8) according to <5> by a dehydration reaction:

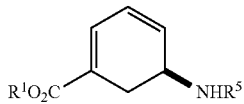

General Formula (9)

wherein $R^1$ represents any of a protective group of a carboxyl group, and a hydrogen atom, and $R^5$ represents any of a protective group of an amino group, and a hydrogen atom.

<12> A method for producing a compound represented by the following general formula (9), the method including in an order mentioned:

reacting together a compound represented by the following general formula (2), a compound represented by the following general formula (3), and a compound represented by the following general formula (4) to provide the compound represented by the general formula (1) according to <1>, reducing a triple bond of the compound represented by the general formula (1) to a double bond to provide the compound represented by the general formula (5) according to <2>, cyclizing the compound represented by the general formula (5) to provide the compound represented by the general formula (6) according to <3>, reducing a carbonyl group of the compound represented by the general formula (6) to a hydroxyl group to provide the compound represented by the general formula (7) according to <4>, converting an $NR^2R^3$ group of the compound represented by the general formula (7) to an $NHR^5$ group, wherein $R^5$ is a protective group of an amino group, and the protective group $R^5$ is different from $R^2$ and $R^3$, to provide the compound represented by the general formula (8) according to <5>, and dehydrating the compound represented by the general formula (8) by a dehydration reaction to provide the compound represented by the following general formula (9):

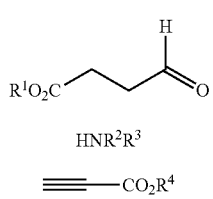

General Formula (2)

General Formula (3)

General Formula (4)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom,

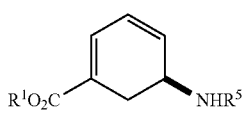

General Formula (9)

wherein $R^1$ represents any of a protective group of a carboxyl group, and a hydrogen atom, and $R^5$ represents any of a protective group of an amino group, and a hydrogen atom.

<13> A method for producing oseltamivir phosphate, the method including:

the method for producing the compound represented by the general formula (1) according to <6>, the method for producing the compound represented by the general formula (5) according to <7>, the method for producing the compound represented by the general formula (6) according to <8>, the method for producing the compound represented by the general formula (7) according to <9>, the method for producing the compound represented by the general formula (8) according to <10>, or the method for producing the compound represented by the general formula (9) according to <11>, or any combination thereof.

What is claimed is:
1. A compound represented by the following general formula (1):

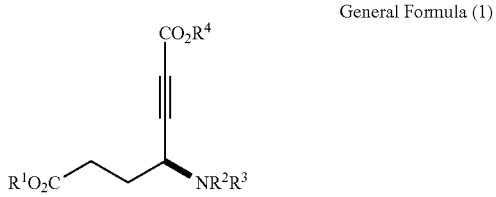

General Formula (1)

wherein $R^1$ represents any of a protective group of a carboxyl group, and a hydrogen atom, $R^2$ and $R^3$ each independently represent any of a protective group of an amino group, and a hydrogen atom, and $R^1$ represents any of a protective group of a carboxyl group, and a hydrogen atom.

2. A compound represented by the following general formula (5):

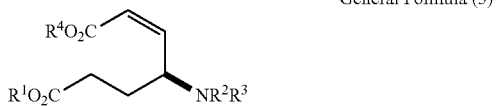

General Formula (5)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

3. A method for producing a compound represented by the following general formula (1), the method comprising:

reacting together a compound represented by the following general formula (2), a compound represented by the following general formula (3), and a compound represented by the following general formula (4):

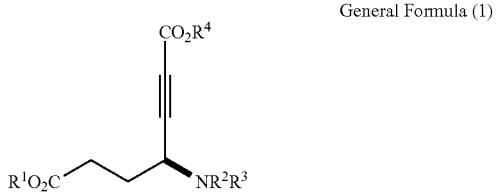

General Formula (1)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom,

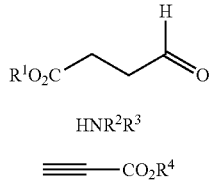

General Formula (2)

General Formula (3)

General Formula (4)

wherein $R^1$ represents any of a protective group of a carboxyl group, and a hydrogen atom, $R^2$ and $R^3$ each independently represent any of a protective group of an amino group, and a hydrogen atom, and $R^4$ represents any of a protective group of a carboxyl group, and a hydrogen atom.

* * * * *